US008768042B2

(12) United States Patent  
Kanagawa et al.

(10) Patent No.: US 8,768,042 B2  
(45) Date of Patent: Jul. 1, 2014

(54) RADIOGRAPHIC IMAGE CAPTURING SYSTEM AND METHOD OF DISPLAYING RADIOGRAPHIC IMAGES

(75) Inventors: Eiichi Kanagawa, Ashigarakami-gun (JP); Noriaki Ida, Ashigarakami-gun (JP); Sadato Akahori, Ashigarakami-gun (JP); Yasunori Ohta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 338 days.

(21) Appl. No.: 13/040,734

(22) Filed: Mar. 4, 2011

(65) Prior Publication Data

US 2011/0222758 A1 Sep. 15, 2011

(30) Foreign Application Priority Data

Mar. 10, 2010 (JP) ................................ 2010-052760

(51) Int. Cl.  
*G06K 9/00* (2006.01)

(52) U.S. Cl.  
USPC ........... 382/154; 382/128; 382/131; 382/132; 382/282; 378/4; 378/11; 378/21; 378/41

(58) Field of Classification Search  
USPC ......... 382/128, 131, 132, 154, 276, 282, 285; 378/4, 11, 21–27, 41, 62, 64  
See application file for complete search history.

(56) References Cited

U.S. PATENT DOCUMENTS

| | | | |
|---|---|---|---|
| 5,090,038 A * | 2/1992 | Asahina | 378/41 |
| 5,233,639 A * | 8/1993 | Marks | 378/41 |
| 6,256,372 B1 * | 7/2001 | Aufrichtig et al. | 378/41 |
| 6,317,481 B1 * | 11/2001 | Berestov | 378/41 |
| 6,853,357 B2 * | 2/2005 | Inoue et al. | 382/181 |
| 7,035,371 B2 * | 4/2006 | Boese et al. | 378/41 |
| 7,369,641 B2 * | 5/2008 | Tsubaki et al. | 378/41 |
| 7,577,282 B2 * | 8/2009 | Gkanatsios et al. | 382/128 |
| 7,711,087 B2 | 5/2010 | Mostafavi | |
| 2002/0090058 A1 * | 7/2002 | Yasuda et al. | 378/205 |
| 2002/0154801 A1 | 10/2002 | Ohishi | |
| 2009/0147073 A1 * | 6/2009 | Getty | 348/51 |

FOREIGN PATENT DOCUMENTS

| | | |
|---|---|---|
| JP | 57-203430 A | 12/1982 |
| JP | 09-313471 A | 12/1997 |
| JP | 2000-105297 A | 4/2000 |
| JP | 2002336222 A | 11/2002 |

(Continued)

OTHER PUBLICATIONS

Rejection of the Application, dated Oct. 1, 2013, issued in corresponding JP Application No. 2010-052760, 10 pages in English and Japanese.

*Primary Examiner* — Eric Rush  
(74) *Attorney, Agent, or Firm* — Sughrue Mion, PLLC

(57) ABSTRACT

A radiographic image capturing system includes an image reconstructor for processing a plurality of radiographic images of a subject in order to reconstruct a radiographic tomographic image of the subject, and a monitor for displaying at least the radiographic tomographic image. The radiographic image capturing system also includes a region-of-interest setter for setting a region of interest of the subject on the radiographic images or the radiographic tomographic image, a radiographic image extractor for extracting, from among the radiographic images, two radiographic images for viewing the region of interest by way of stereographic vision, and a first stereographic vision display controller or a second stereographic vision display controller for controlling the monitor to display the extracted two radiographic images for stereographic vision.

17 Claims, 12 Drawing Sheets

(56) References Cited

FOREIGN PATENT DOCUMENTS

| JP | 3494683 | B2 | 11/2003 |
| JP | 2006-212056 | A | 8/2006 |
| JP | 2007-130487 | A | 5/2007 |
| JP | 2008-043757 | A | 2/2008 |
| JP | 2009-533086 | A | 9/2009 |

\* cited by examiner

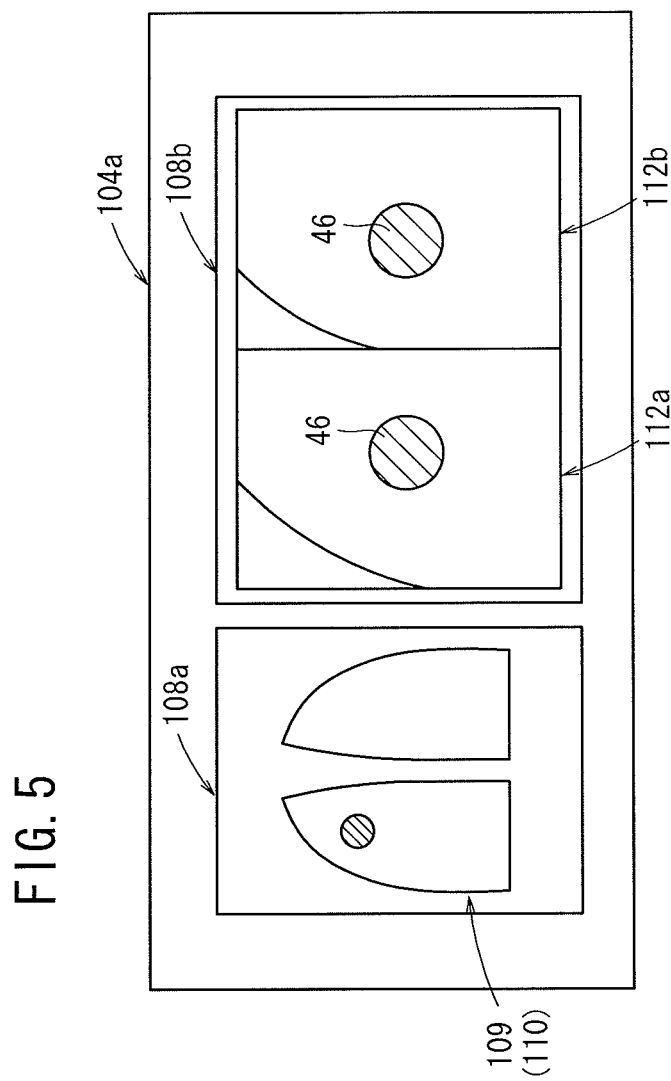

RADIOGRAPHIC IMAGE CAPTURING SYSTEM AND METHOD OF DISPLAYING RADIOGRAPHIC IMAGES

CROSS-REFERENCE TO RELATED APPLICATION

This application is based upon and claims the benefit of priority from Japanese Patent Application No. 2010-052760 filed on Mar. 10, 2010, of which the contents are incorporated herein by reference.

BACKGROUND OF THE INVENTION

1. Field of the Invention

The present invention relates to a radiographic image capturing system for acquiring a tomographic image according to radiographic image capturing processes, and a method of displaying radiographic images.

2. Description of the Related Art

In recent years, in order for an X-ray image capturing apparatus to make a detailed observation of a local region of a subject, there has been proposed a tomosynthesis image capturing process for moving an X-ray tube over the subject while applying radiation from the X-ray tube to the subject at different angles thereby to capture radiographic images of the subject. The captured radiographic images are added together to generate a tomographic image, which is representative, with emphasis, of a desired sectional plane across the subject (see, for example, Japanese Laid-Open Patent Publication No. 57-203430).

In a tomosynthesis image capturing process, a plurality of radiographic images of a subject, which are captured at different angles, are acquired by moving an X-ray tube parallel to a detector such as a flat panel or the like, or by moving the X-ray tube along a circular or elliptical arcuate path, and the acquired radiographic images are processed to reconstruct a tomographic image of the subject. The tomographic image can be generated by translating the radiographic images, adjusting sizes of the radiographic images, and adding them together (see, for example, Japanese Laid-Open Patent Publication No. 2008-043757).

Tomosynthesis image capturing processes are disclosed in Japanese Laid-Open Patent Publication No. 2009-533086 (PCT), Japanese Laid-Open Patent Publication No. 09-313471, Japanese Laid-Open Patent Publication No. 2006-212056, and Japanese Laid-Open Patent Publication No. 2007-130487, for example.

According to the process disclosed in Japanese Laid-Open Patent Publication No. 2009-533086 (PCT), a system, which is capable of capturing both an image and a tomosynthesis image of a subject, determines the position and shape of the subject from the tomosynthesis image, and captures a CT image of the subject based on the determined position and shape of the subject.

According to the process disclosed in Japanese Laid-Open Patent Publication No. 09-313471, regions corresponding to a left-eye image and a right-eye image for three-dimensional vision (stereographic vision) are established in order to control exposure conditions for the left-eye image and the right-eye image.

According to the process disclosed in Japanese Laid-Open Patent Publication No. 2006-212056, transmissive radiographic images, which have been captured, are processed in order to reconstruct a three-dimensional image. After parameters are extracted from the three-dimensional image, positions of a radiation source for capturing images for stereographic vision are determined, and then the images are captured.

According to the process disclosed in Japanese Laid-Open Patent Publication No. 2007-130487, a pair of projected images extracted from a tomographic projection data set are used as a left-eye image and a right-eye image for stereographic vision. Japanese Laid-Open Patent Publication No. 2007-130487 describes the usefulness of an observation process based on stereographic vision, stating that a three-dimensional observation process, i.e., an observation process based on stereographic vision, is useful during observation of radiographic images because the process can provide clues concerning distance or depth, in the same manner as human eyes in a normal process of visual perception, and hence can clarify relative spatial relationships between objects in a subject's body.

The process disclosed in Japanese Laid-Open Patent Publication No. 2009-533086 (PCT) is problematic in that the dose of radiation applied to the subject is large because it is necessary to perform a tomosynthesis image capturing process on the subject prior to a CT image capturing process.

Japanese Laid-Open Patent Publication No. 09-313471 discloses a process of capturing radiographic images for producing images for observation based on stereographic vision. If a tomographic image is generated separately from images for stereographic vision, then it is necessary to perform a radiographic image capturing process in order to produce the tomographic image. In this case, the dose of radiation applied to the subject increases.

The process disclosed in Japanese Laid-Open Patent Publication No. 2006-212056 also is disadvantageous in that, after a radiographic image capturing process has been performed to produce a three-dimensional image, image capturing conditions for stereographic vision are determined based on information of the three-dimensional image, and then a radiographic image capturing process for stereographic vision is carried out. Therefore, the dose of radiation applied to the subject also increases.

The process disclosed in Japanese Laid-Open Patent Publication No. 2007-130487 is able to solve problems encountered using the processes disclosed in Japanese Laid-Open Patent Publication No. 2009-533086 (PCT), Japanese Laid-Open Patent Publication No. 09-313471, and Japanese Laid-Open Patent Publication No. 2006-212056, because the process disclosed in Japanese Laid-Open Patent Publication No. 2007-130487 uses a pair of radiographic images extracted from tomographic image data.

However, according to the process disclosed in Japanese Laid-Open Patent Publication No. 2007-130487, the pair of radiographic images are simply selected and displayed. There is no specific technique relating to extraction and display of radiographic images for stereographic vision when the operator wants to confirm a lesion area by away of stereographic vision, after having first confirmed a tomographic image. Therefore, the disclosed process is disadvantageous in that it is inconvenient for viewing images by way of stereographic vision.

SUMMARY OF THE INVENTION

An object of the present invention is to provide a radiographic image capturing system and a method of displaying radiographic images, which are convenient for viewing images by way of stereographic vision, and which make it possible to promote the widespread use of image observations by way of stereographic vision, while at the same time preventing subjects to be imaged from being exposed to an increased dose of radiation.

According to a first aspect of the present invention, there is provided a radiographic image capturing system comprising a radiation detecting device, a radiographic image acquirer for moving a radiation irradiator disposed in confronting relation to the radiation detecting device successively to a plurality of positions, and controlling the radiation irradiator to apply radiation from the positions along respective different directions to a subject disposed over the radiation detecting device, for acquiring a plurality of respective radiographic images from the radiation detecting device, an image reconstructor for processing the radiographic images acquired by the radiographic image acquirer to reconstruct a radiographic tomographic image of the subject, a display device for displaying at least the radiographic images, a region-of-interest setter for setting a region of interest of the subject for stereographic vision, a radiographic image extractor for extracting, from among the radiographic images, two radiographic images for viewing the region of interest by way of stereographic vision, and a stereographic vision display controller for controlling the display device to display the extracted two radiographic images for stereographic vision.

In the first aspect of the present invention, the radiographic image capturing system further comprises an input device operable by an operator of the radiographic image capturing system, and an image display controller for controlling the display device to display a radiographic image, which is selected from among the radiographic images acquired by the radiographic image acquirer, based on an operation input signal from the input device, wherein the region-of-interest setter sets the region of interest on the selected radiographic image.

In the first aspect of the present invention, the radiographic image capturing system further comprises an input device operable by an operator of the radiographic image capturing system, and an image display controller for controlling the display device to display a radiographic tomographic image of a body section of the subject, which is selected from among radiographic tomographic images reconstructed by the image reconstructor, based on an operation input signal from the input device, wherein the region-of-interest setter sets the region of interest on the selected radiographic tomographic image.

In the first aspect of the present invention, the radiographic image extractor comprises a first position determiner for deciding on one position serving as a center for stereographic vision from among the positions from which the radiation irradiator applies radiation, based on coordinates of the region of interest, and a second position determiner for deciding on two positions, which are positionally symmetric with respect to the one position decided on by the first position determiner, from among the positions from which the radiation irradiator applies radiation, wherein the radiographic image extractor extracts, as said two radiographic images, radiographic images generated when the radiation irradiator applies radiation from the two positions, from among the radiographic images acquired by the radiographic image acquirer.

In the first aspect of the present invention, the first position determiner comprises a coordinate-of-interest calculator for determining plane coordinates on the radiation detecting device, which correspond to the coordinates of the region of interest, wherein the first position determiner decides on a position, plane coordinates of which are closest to the determined plane coordinates on the radiation detecting device, from among the positions from which the radiation irradiator applies radiation, as the one position serving as the center for stereographic vision.

In the first aspect of the present invention, the second position determiner comprises a reference coordinate calculator for determining plane coordinates as reference coordinates on the radiation detecting device, which correspond to the one position as the center for stereographic vision, wherein the second position determiner decides on two positions, which are positionally symmetric with respect to the one position, and which are connected to the reference coordinates by respective straight lines that are angularly spaced a preset angle from a straight line interconnecting the one position and the reference coordinates, from among the positions from which the radiation irradiator applies radiation, as two positions for stereographic vision.

In the first aspect of the present invention, the second position determiner decides on two positions, where aspect ratios defined from a vertical distance from the one position to the radiation detecting device and horizontal distances from the one position to the positions from which the radiation irradiator applies radiation satisfy a preset aspect ratio, as two positions for stereographic vision.

In the first aspect of the present invention, the radiographic image capturing system further comprises an input device operable by an operator of the radiographic image capturing system, wherein the second position determiner comprises an initial selector for initially selecting two positions closest to the one position as two positions for stereographic vision, and an updating selector for selecting two positions adjacent to the initially selected two positions as two updated positions for stereographic vision based on an operation input signal for updating to next positions from the input device, and wherein the second position determiner decides on the selected two positions as two positions for stereographic vision based on an operation input signal for deciding from the input device.

In the first aspect of the present invention, the image display controller controls the display device to switch between displaying the selected radiographic image and displaying the extracted two radiographic images, based on an operation input signal from the input device.

In the first aspect of the present invention, the image display controller controls the display device to display the selected radiographic image in a first display area, and the image display controller controls the display device to display the extracted two radiographic images in a second display area.

In the first aspect of the present invention, the image display controller controls the display device to switch between displaying the selected radiographic image and displaying the extracted two radiographic images, based on an operation input signal from the input device.

In the first aspect of the present invention, the image display controller controls the display device to display the selected radiographic image in a first display area, and the stereographic vision display controller controls the display device to display the extracted two radiographic images in a second display area.

In the first aspect of the present invention, the radiographic image capturing system further comprises an input device operable by an operator of the radiographic image capturing system, wherein the region-of-interest setter sets the region of interest based on an operation input signal from the input device.

According to a second aspect of the present invention, there is also provided a method of displaying radiographic images in a radiographic image capturing system including a radiation detecting device, a radiographic image acquirer for moving a radiation irradiator disposed in confronting relation to the radiation detecting device successively to a plurality of positions, and controlling the radiation irradiator to apply radiation from the positions along respective different directions to a subject disposed over the radiation detecting device, for acquiring a plurality of respective radiographic images from the radiation detecting device, an image reconstructor for processing the radiographic images acquired by the radiographic image acquirer to reconstruct a radiographic tomographic image of the subject, and a display device for displaying at least the radiographic images, the method comprising the steps of setting a region of interest of the subject for stereographic vision, extracting, from among said radiographic images, two radiographic images for viewing the region of interest by way of stereographic vision, and controlling the display device to display the extracted two radiographic images for stereographic vision.

In the second aspect of the present invention, the radiographic image capturing system includes an input device operable by an operator of the radiographic image capturing system, the method further comprising the step of controlling the display device to display a radiographic image, which is selected from among the radiographic images acquired by the radiographic image acquirer, based on an operation input signal from the input device, wherein the step of setting the region of interest sets the region of interest on the selected radiographic image.

In the second aspect of the present invention, the radiographic image capturing system includes an input device operable by an operator of the radiographic image capturing system, the method further comprising the step of controlling the display device to display a radiographic tomographic image of a body section of the subject, which is selected from radiographic tomographic images reconstructed by the image reconstructor, based on an operation input signal from the input device, wherein the step of setting the region of interest sets the region of interest on the selected radiographic tomographic image.

In the second aspect of the present invention, the method further comprises the step of controlling the display device to switch between displaying the selected radiographic image and displaying the extracted two radiographic images, based on an operation input signal from the input device.

In the second aspect of the present invention, the step of controlling the display device to display a radiographic image displays the selected radiographic image in a first display area, and the step of controlling the display device to display the extracted two radiographic images displays the extracted two radiographic images in a second display area.

In the second aspect of the present invention, the method further comprises the step of controlling the display device to switch between displaying the selected radiographic image and displaying the extracted two radiographic images, based on an operation input signal from the input device.

In the second aspect of the present invention, the step of controlling the display device to display a radiographic image displays the selected radiographic image in a first display area, and the step of controlling the display device to display the extracted two radiographic images displays the extracted two radiographic images in a second display area.

The radiographic image capturing system and the method of displaying radiographic images according to the present invention are convenient for viewing images by way of stereographic vision, and make it possible to promote the widespread use of image observations by way of stereographic vision, while at the same time preventing subjects to be imaged from being exposed to an increased dose of radiation.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 5 is a diagram showing by way of example a first observational screen displayed on a monitor;

DESCRIPTION OF THE PREFERRED EMBODIMENTS

A radiographic image capturing system and a method of displaying radiographic images according to a preferred embodiment of the present invention will be described in detail below with reference to FIGS. 1 through 12.

Figure 1:
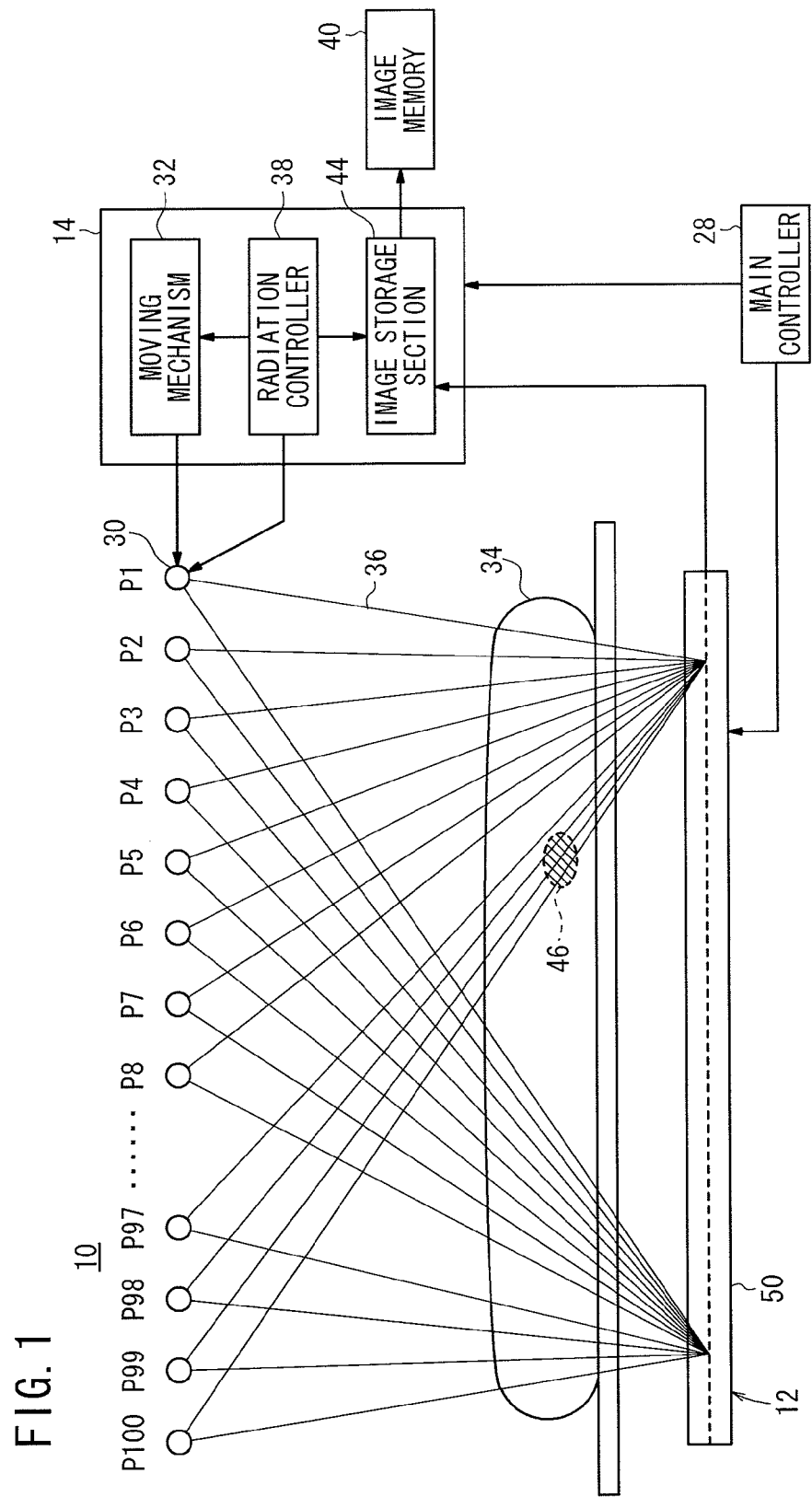
FIG. 1 is a schematic diagram, partially in block form, of a radiographic image capturing system according to an embodiment of the present invention.
Figure 2:
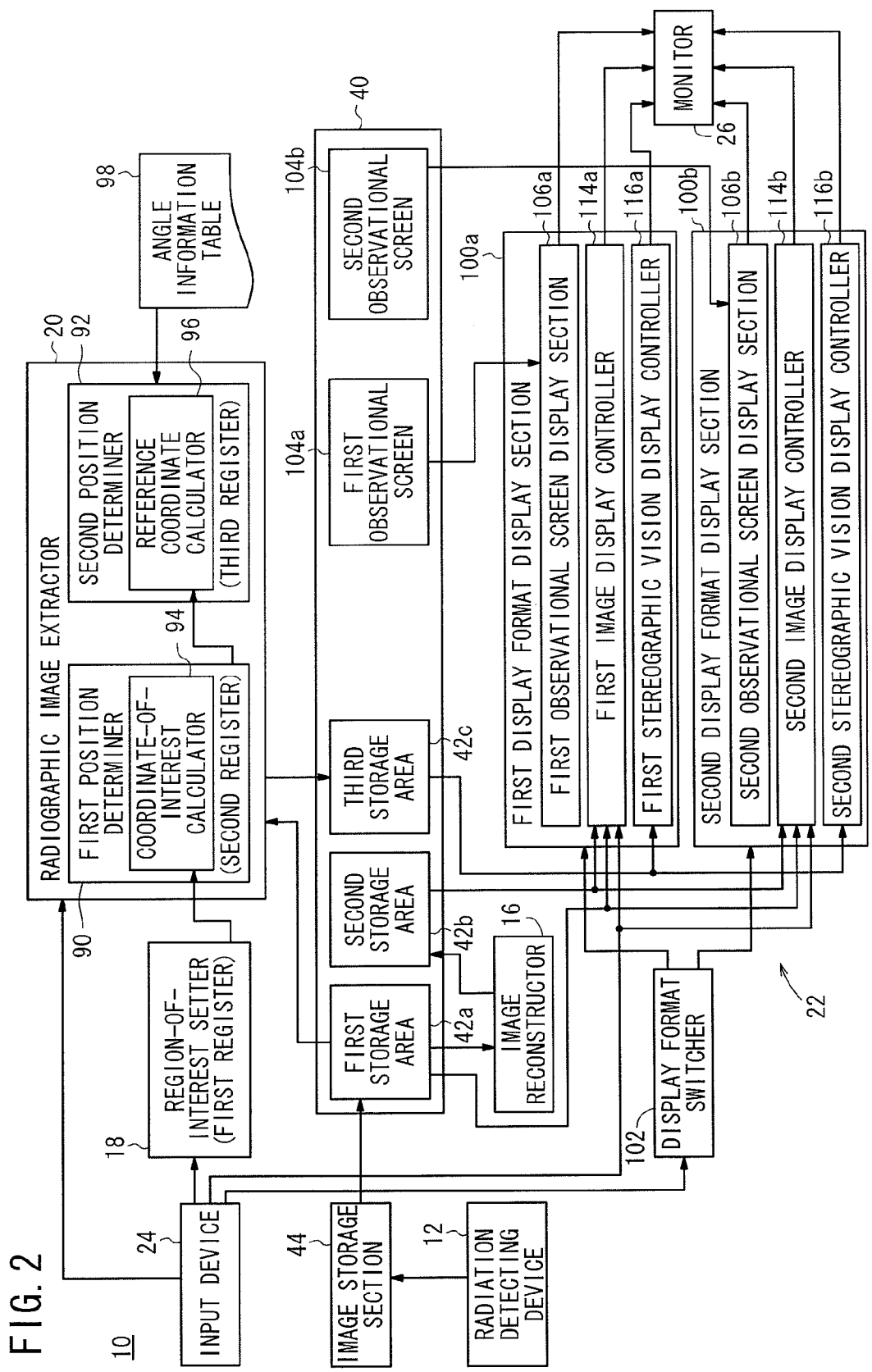
FIG. 2 is a block diagram of a region-of-interest setter, a radiographic image extractor, and an image display controller according to the embodiment of the present invention.

As shown in FIGS. 1 and 2, a radiographic image capturing system 10 according to a preferred embodiment of the present invention comprises a radiation detecting device 12, a radiographic image acquirer 14, an image reconstructor 16, a region-of-interest setter 18, a radiographic image extractor 20, an image display controller 22, an input device 24, a monitor 26, and a main controller 28 for controlling the aforementioned components. The main controller 28 has been omitted from illustration in FIG. 2.

As shown in FIG. 1, the radiographic image acquirer 14 comprises a radiation irradiator 30 movably disposed in confronting relation to the radiation detecting device 12, a moving mechanism 32 for moving the radiation irradiator 30 successively to a plurality of preset positions P1, P2, P3, . . . over the radiation detecting device 12, a radiation controller 38 for controlling the radiation irradiator 30 to apply radiation 36 to a subject 34 over the radiation detecting device 12 when the radiation irradiator 30 has reached each of the preset positions P1, P2, P3, . . . , and an image storage section 44 for storing radiographic images (raw data) sent successively from the radiation detecting device 12 as a chronological sequence of radiographic images, for example, in a first storage area 42a (see FIG. 2) of an image memory 40. The radiographic image acquirer 14 operates by moving the radiation irradiator 30 successively to the preset positions P1, P2, P3, . . . applying radiation 36 from the radiation irradiator 30 at the preset positions P1, P2, P3, . . . along respective different directions toward the subject 34 over the radiation detecting device 12, and acquiring a plurality of respective radiographic images from the radiation detecting device 12.

Image capturing processes that are carried out by the radiographic image acquirer 14 include an individual image capturing process, which is performed when the radiation irradiator 30 has reached each of the preset positions P1, P2, P3, . . . , and a collective image capturing process, which is representative of an overall individual image capturing process. The individual image capturing process will hereinafter be referred to as a "radiographic image capturing process," and the collective image capturing process as a "tomosynthesis image capturing process."

The image reconstructor 16 processes a plurality of radiographic images stored in the first storage area 42a of the image memory 40 in order to reconstruct a tomographic image of the subject 34, in particular a tomographic image of a region 46 of interest of the subject 34, along a plane parallel to a detecting surface of the radiation detecting device 12, and stores the reconstructed tomographic image in a second storage area 42b of the image memory 40. The image reconstructor 16 may reconstruct a tomographic image according to a reconstructing process, such as a simple backprojection process or a filtered backprojection process, for example. The simple backprojection process is a process for backprojecting a plurality of radiographic images without applying a reconstruction filter, and then adding the radiographic images into a reconstructed image. There are two types of filtered backprojection processes, i.e., a process for applying a reconstruction filter as a convolution filter to a plurality of radiographic images, backprojecting the radiographic images, and then adding the radiographic images into a reconstructed image, and a process of Fourier-transforming a plurality of radiographic images into frequency-domain data, applying a reconstruction filter to the frequency-domain data, backprojecting the frequency-domain data, and thereafter adding the radiographic images into a reconstructed image. Either of these filtered backprojection processes may be employed. The simple backprojection process and the filtered backprojection process will be referred to collectively as a "backprojection process."

The radiation detecting device 12 includes a casing 50 (see FIG. 1), a battery 52 (see FIG. 3), a radiation detector 54, and a detector controller 56, all of which are housed in the casing 50.

Figure 3:
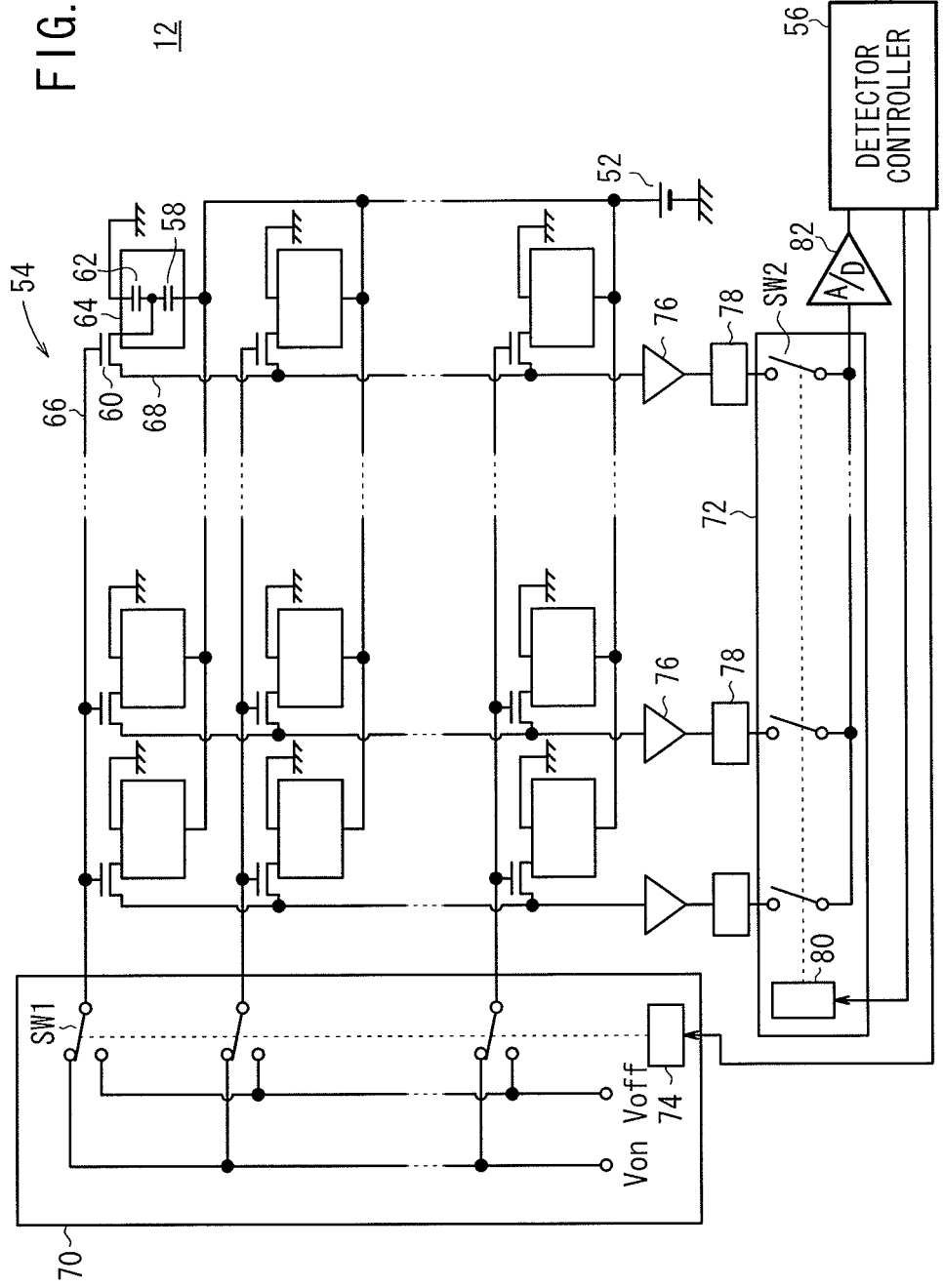
FIG. 3 is a circuit diagram, partially in block form, of a radiation detector in a radiation detecting apparatus, which is incorporated in the radiographic image capturing system according to the embodiment of the present invention.

As shown in FIG. 3, the radiation detector 54 comprises an array of thin-film transistors (TFTs) 60 arranged in rows and columns, a photoelectric conversion layer 58 made of a material such as amorphous selenium (a-Se) for generating electric charges upon detection of radiation 36 (see FIG. 1), the photoelectric conversion layer 58 being disposed on the array of TFTs 60, and an array of storage capacitors 62 connected to the photoelectric conversion layer 58. When radiation 36 is applied to the radiation detector 54, the photoelectric conversion layer 58 generates electric charges, and the generated electric charges are stored in storage capacitors 62. Then, the TFTs 60 are turned on, each row at a time, in order to read the electric charges from the storage capacitors 62 as an image signal. In FIG. 3, the photoelectric conversion layer 58 and one of the storage capacitors 62 are shown as making up a pixel 64, wherein the pixel 64 is connected to one of the TFTs 60. Details of the other pixels 64 have been omitted from illustration. Since amorphous selenium tends to change in structure and lose functions thereof at high temperatures, amorphous selenium needs to be used within a certain temperature range. Therefore, some means should preferably be provided in the casing 50 for cooling the radiation detector 54.

The TFTs 60 connected to the respective pixels 64 are also connected to respective gate lines 66 extending parallel to the rows, and to respective signal lines 68 extending parallel to the columns. The gate lines 66 are connected to a line scanning driver 70, and the signal lines 68 are connected to a multiplexer 72 that serves as a reading circuit.

The gate lines 66 are supplied with control signals Von, Voff for turning on and off the TFTs 60 along rows from the line scanning driver 70. The line scanning driver 70 comprises a plurality of first switches SW1 for switching between the gate lines 66, and a row address decoder 74 for outputting a selection signal for selecting one of the first switches SW1 at a time. The row address decoder 74 is supplied with an address signal from the detector controller 56.

The signal lines 68 are supplied with electric charges stored in the storage capacitors 62 of the pixels 64 through the TFTs 60 arranged in the columns. Electric charges supplied to the signal lines 68 are amplified by amplifiers 76 connected respectively to the signal lines 68. The amplifiers 76 are connected through respective sample and hold circuits 78 to the multiplexer 72. The multiplexer 72 comprises a plurality of second switches SW2 for successively switching between the signal lines 68, and a column address decoder 80 for outputting a selection signal for selecting one of the second switches SW2 at a time. The column address decoder 80 is supplied with an address signal from the detector controller 56. The multiplexer 72 has an output terminal connected to an A/D converter 82. A radiographic image signal generated by the multiplexer 72 based on electric charges from the sample and hold circuits 78 is converted by the A/D converter 82 into a digital image signal representative of radiographic image information, which is supplied to the detector controller 56. The detector controller 56 supplies the digital image signal to the image memory 40 (see FIG. 2), which stores the supplied digital image signal in the first storage area 42a. In summary, each time the radiographic image capturing system 10 performs a radiographic image capturing process, the radiation detecting device 12 outputs a radiographic image. Radiographic images, which are successively output from the radiation detecting device 12, are stored in the first storage area 42a of the image memory 40 in chronological order, for example.

The region-of-interest setter 18 shown in FIG. 2 sets a region 46 of interest on a radiographic image or on a radiographic tomographic image based on an operation input signal from the input device 24. More specifically, the region-of-interest setter 18 sets a region 46 of interest in the following manner. While confirming a radiographic image or a radiographic tomographic image displayed on the monitor 26, for example, the operator, e.g., a doctor or a radiological technician, of the radiographic image capturing system 10 displays a frame, e.g., a rectangular frame, a circular frame, or the like, around the image of the region 46 of interest with a coordinate input unit such as a mouse or the like of the input device 24, and decides on the frame by left-clicking the mouse, thereby determining the two-dimensional coordinates of the center of the frame as coordinates of the region 46 of interest, and registering the coordinates of the region 46 in a first register. If the frame is a rectangular frame, then the two-dimensional coordinates of a point of intersection of two diagonal lines, for example, of the rectangular frame are registered in the first register. If the frame is a circular frame, then the two-dimensional coordinates of a center of the circular frame are registered in the first register. The two-dimensional coordinates represent coordinates on radiographic images or radiographic tomographic images. The two-dimensional coordinates are stored in the image memory 40.

The radiographic image extractor 20 comprises a first position determiner 90 and a second position determiner 92. The radiographic image extractor 20 extracts two radiographic images for constructing the region 46 of interest viewable for stereographic vision (three-dimensional vision) from a plurality of radiographic images that are stored in the first storage area 42a of the image memory 40.

The first position determiner 90 decides on a position (central position) serving as a center for stereographic vision from among the positions P1, P2, P3, . . . from which the radiation irradiator 30 applies radiation 36, based on the coordinates of the region 46 of interest, i.e., the two-dimensional coordinates registered in the first register, on a radiographic image or on a radiographic tomographic image. More specifically, the first position determiner 90 has a coordinate-of-interest calculator 94 for determining plane coordinates on the radiation detecting device 12, which correspond to the coordinates of the region 46 of interest on the radiographic image or on the radiographic tomographic image. The plane coordinates refer to coordinates among spatial coordinates, except for heightwise coordinates. The first position determiner 90 decides on a position (e.g., the position P5 shown in FIG. 4) among the positions P1, P2, P3, . . . , the plane coordinates of which are closest to plane coordinates Pc (see FIG. 4) on the radiation detecting device 12, which are produced by the coordinate-of-interest calculator 94, as a position (central position) serving as a center for stereographic vision. The plane coordinates of the determined central position are registered in a second register.

The second position determiner 92 decides on two positions, which are positionally symmetric with respect to the central position determined by the first position determiner 90, from among the positions P1, P2, P3, . . . .

Figure 4:
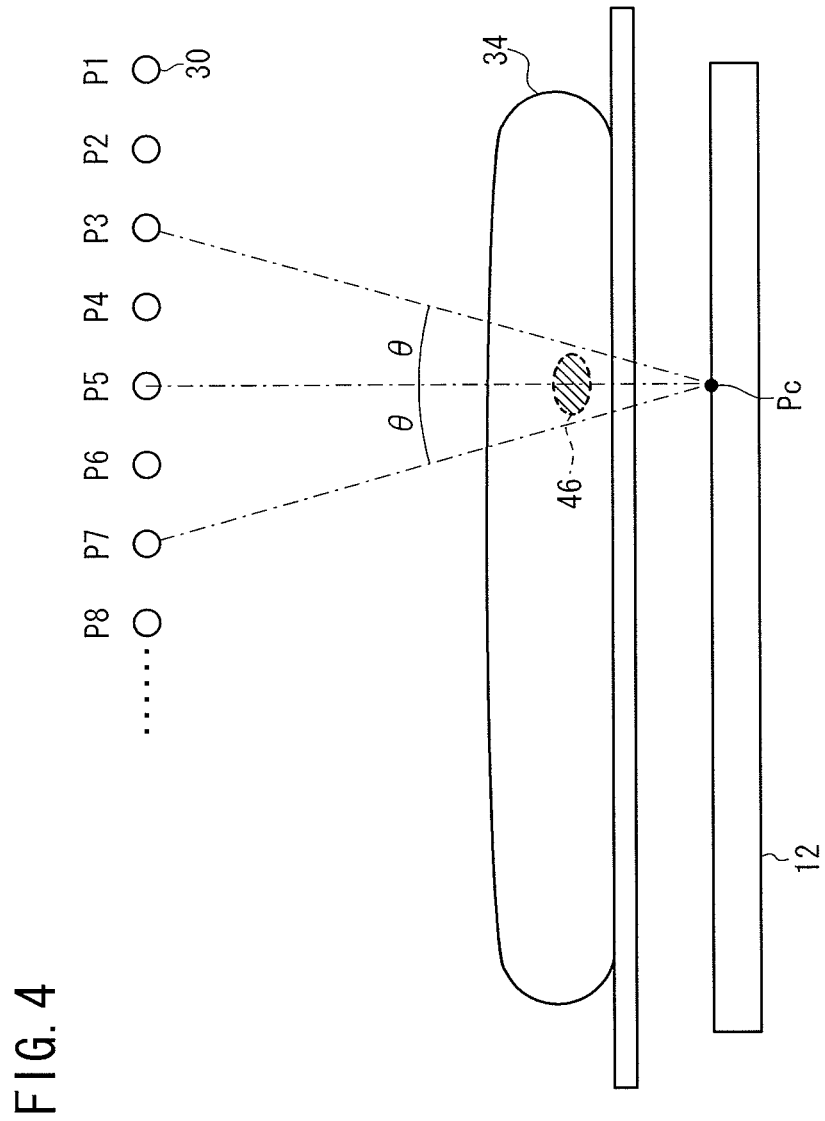
FIG. 4 is a schematic diagram illustrative of a process of determining two positions, i.e., a left-eye position and a right-eye position, with a second position determiner according to the embodiment of the present invention.

More specifically, the second position determiner 92 has a reference coordinate calculator 96 for determining plane coordinates (reference coordinates: the coordinates Pc in FIG. 4) on the radiation detecting device 12, which correspond to the central position that serves as the center for stereographic vision. The second position determiner 92 decides on two positions, from among the positions P1, P2, P3, . . . , which are positionally symmetric with respect to the central position (the position P5 in FIG. 4), and which are connected to the reference coordinates (the coordinates Pc in FIG. 4) determined by the reference coordinate calculator 96 by respective straight lines that are angularly spaced a preset angle θ from a straight line interconnecting the central position and the reference coordinates, as two positions for stereographic vision, i.e., a left-eye position and a right-eye position. In FIG. 4, the positions P3, P7, for example, are determined as a left-eye position and a right-eye position. Plane coordinates of the left-eye position and the right-eye position are registered in a third register.

Since the distance between the left and right eyes varies from individual to individual, the angle θ is established depending on the doctor who observes images by way of stereographic vision. If there are several doctors who observe images by way of stereographic vision on the radiographic image capturing system 10, then an angle information table 98, which registers therein ID codes and angles θ of the respective doctors, is combined with the radiographic image extractor 20. The second position determiner 92 then reads an angle θ depending on an ID code that is entered through the input device 24, i.e., the ID code of the doctor who presently observes images by way of stereographic vision, from the angle information table 98, and determines a left-eye position and a right-eye position based on the read angle θ in the manner described above.

The radiographic image extractor 20 extracts two radiographic images produced when the radiation irradiator 30 emits radiation 36 toward the subject 34 from the left-eye position and the right-eye position, from among the radiographic images stored in the first storage area 42a of the image memory 40, as radiographic images for stereographic vision, i.e., a left-eye radiographic image and a right-eye radiographic image, and stores the left-eye radiographic image and the right-eye radiographic image in a third storage area 42c of the image memory 40.

The image display controller 22 comprises a first display format display section 100a, a second display format display section 100b, and a display format switcher 102.

The display format switcher 102 activates the first display format display section 100a based on an input signal requesting a first display format from the input device 24, and activates the second display format display section 100b based on an input signal requesting a second display format from the input device 24.

The first display format display section 100a includes a first observational screen display section 106a for displaying a first observational screen 104a. As shown in FIG. 5, the first observational screen 104a includes a first display area 108a on the left side, and a second display area 108b on the right side. The first display area 108a displays a radiographic image 109 or a radiographic tomographic image 110, which may be selected by the operator using the input device 24. The second display area 108b displays a left-eye radiographic image 112a on the left side and a right-eye radiographic image 112b on the right side. The first display format display section 100a includes, in addition to the first observational screen display section 106a, a first image display controller 114a for displaying a radiographic image 109 or a radiographic tomographic image 110 in the first display area 108a, and a first stereographic vision display controller 116a for displaying a left-eye radiographic image 112a on the left side of the second display area 108b, and for displaying a right-eye radiographic image 112b on the right side of the second display area 108b.

Figure 6A:
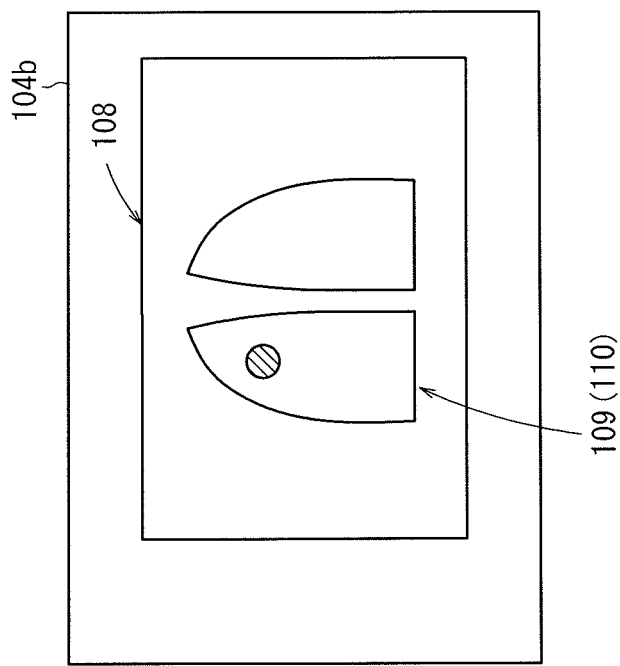
FIGS. 6A and 6B are diagrams showing by way of example a second observational screen displayed on the monitor.
Figure 6B:
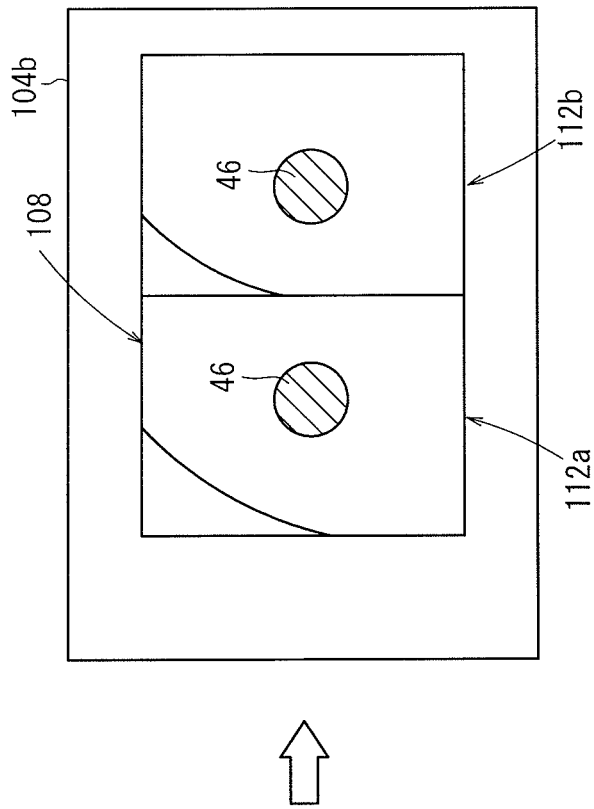

Similarly, the second display format display section 100b includes a second observational screen display section 106b for displaying a second observational screen 104b. As shown in FIGS. 6A and 6B, the second observational screen 104b includes a display area 108. The display area 108 selectively displays a radiographic image 109 or a radiographic tomographic image 110 (see FIG. 6A), which is selected by the operator using the input device 24, and images for stereographic vision, i.e., a left-eye radiographic image 112a and a right-eye radiographic image 112b (see FIG. 6B). The second display format display section 100b also includes, in addition to the second observational screen display section 106b, a second image display controller 114b for displaying a radiographic image 109 or a radiographic tomographic image 110 in the display area 108, and a second stereographic vision display controller 116b for displaying a left-eye radiographic image 112a on the left side of the display area 108, and for displaying a right-eye radiographic image 112b on the right side of the display area 108.

The radiographic image capturing system 10 is basically constructed as described above. Operations of the radiographic image capturing system 10 will be described below with reference to FIG. 7.

Figure 7:
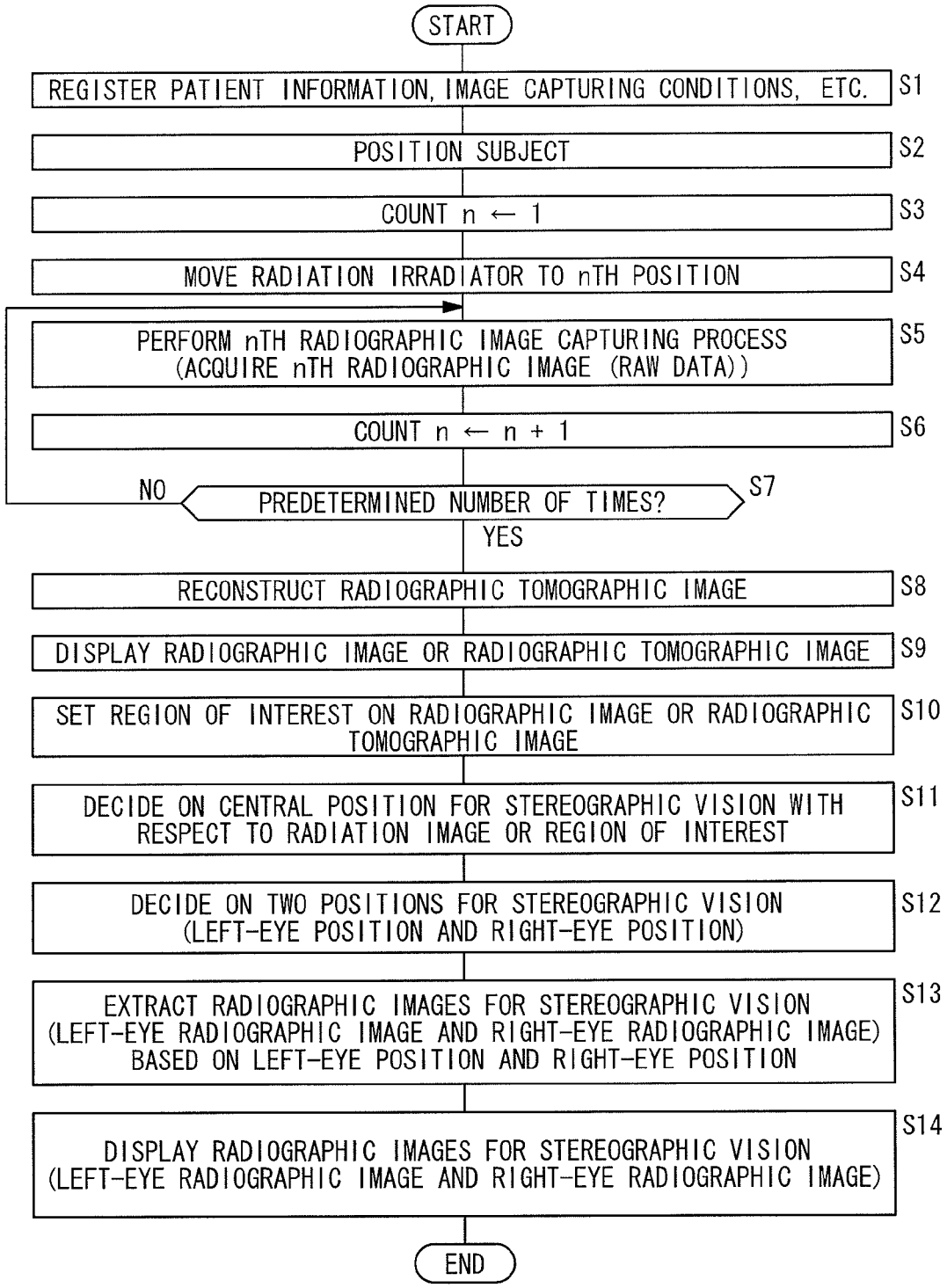
FIG. 7 is a flowchart of an operation sequence of the radiographic image capturing system according to the embodiment of the present invention.

In step S1 shown in FIG. 7, patient information of a patient, i.e., the subject 34 to be imaged, is registered in the main controller 28 before images of the subject 34 are captured. If image capturing conditions, including a body region to be imaged and an image capturing method, are known, then such image capturing conditions also are registered in the main controller 28.

Then, in step S2, the subject 34 is guided to the radiographic image capturing system 10. The subject 34 is positioned in the radiographic image capturing system 10 depending on a body region to be imaged, etc.

After the subject 34 has been positioned, control proceeds to step S3, and the radiographic image capturing system 10 starts a tomosynthesis image capturing process based on an instruction, which the operator gives to the main controller 28. More specifically, in step S3, a count n is reset to "1". Then, in step S4, the radiation controller 38 of the radiographic image acquirer 14 controls the moving mechanism 32 to move the radiation irradiator 30 to an nth position, which initially is the position P1. When the radiation irradiator 30 reaches the nth position, control proceeds to step S5 in which the radiographic image capturing system 10 performs an nth radiographic image capturing process. An nth radiographic image generated in the nth radiographic image capturing process is stored in the first storage area 42a of the image memory 40. In this manner, the radiographic image acquirer 14 acquires the nth radiographic image. Thereafter, the count n is incremented by +1 in step S6. In step S7, the main controller 28 determines whether or not the radiographic image capturing process has been carried out a predetermined number of times, e.g., 100 times. If the number of times that the radiographic image capturing process has been carried out is smaller than the predetermined number, then control returns to step S5, and steps S5, S6 and S7 are repeated.

If the number of times that the radiographic image capturing process has been carried out reaches the predetermined number in step S7, then control proceeds to step S8. In step S8, the radiographic images generated in the radiographic image capturing process, which has been carried out a predetermined number of times, and which are stored in the first storage area 42a of the image memory 40, are processed in order to reconstruct a radiographic tomographic image 110 (see FIG. 5) of the subject 34 according to a backprojection process. The reconstructed radiographic tomographic image 110 is stored in the second storage area 42b of the image memory 40.

In step S9, the image display controller 22 displays a radiographic image 109 or a radiographic tomographic image 110 on the monitor 26 based on a display request for the radiographic image 109 or the radiographic tomographic image 110, which is selected by an operation input signal from the input device 24. For example, if the display request requests display of a radiographic image 109 or a radiographic tomographic image 110 in the first display format, then the first observational screen display section 106a of the first display format display section 100a displays the first observational screen 104a (see FIG. 5) on the monitor 26. Thereafter, the first image display controller 114a reads a radiographic image 109 or a radiographic tomographic image 110, which has been selected by an operation input signal from the input device 24, from the first storage area 42a or the second storage area 42b of the image memory 40, and displays the selected image in the first display area 108a of the first observational screen 104a. If the display request requests display of a radiographic image 109 or a radiographic tomographic image 110 in the second display format, then the second observational screen display section 106b of the second display format display section 100b displays the second observational screen 104b (see FIG. 6A) on the monitor 26. Thereafter, the second image display controller 114b reads a radiographic image 109 or a radiographic tomographic image 110, which has been selected by an operation input signal from the input device 24, from the first storage area 42a or the second storage area 42b of the image memory 40, and displays the selected image in the display area 108 of the second observational screen 104b.

Then, in step S10, the region-of-interest setter 18 sets a region 46 of interest on the radiographic image 109 or the radiographic tomographic image 110, based on an operation input signal from the input device 24. More specifically, for example, the operator displays a frame, e.g., a rectangular frame, a circular frame, or the like, around an image of the region 46 of interest using a coordinate input unit such as a mouse or the like of the input device 24, while confirming the radiographic image 109 or the radiographic tomographic image 110 displayed on the monitor 26, and decides on the frame by left-clicking the mouse, thereby determining the two-dimensional coordinates of the center of the frame as coordinates of the region 46 of interest.

In step S11, the first position determiner 90 of the radiographic image extractor 20 decides on a position (central position) serving as a center for stereographic vision with respect to the region 46 of interest, from among the positions P1, P2, P3, . . . from which radiation 36 has been applied by the radiation irradiator 30, based on the coordinates of the region 46 of interest, i.e., the two-dimensional coordinates registered in the first register, on the radiographic image 109 or the radiographic tomographic image 110. As described above, the first position determiner 90 decides on a position, from among the positions P1, P2, P3, . . . , plane coordinates of which are closest to the plane coordinates of the region 46 of interest on the radiation detecting device 12, which are produced by the coordinate-of-interest calculator 94, as a position (central position) serving as a center for stereographic vision, and registers the plane coordinates of the determined central position in the second register.

In step S12, the second position determiner 92 of the radiographic image extractor 20 decides on two positions, which are positionally symmetric with respect to the central position, from among a plurality of positions, as two positions for stereographic vision, i.e., a left-eye position and a right-eye position. According to the present embodiment, in particular, the second position determiner 92 decides on two positions, which are positionally symmetric with respect to the central position, and which are connected to the reference coordinates determined by the reference coordinate calculator 96 by respective straight lines that are angularly spaced a preset angle θ from a straight line interconnecting the central position and the reference coordinates, from among a plurality of positions, as two positions for stereographic vision, i.e., a left-eye position and a right-eye position. The determined plane coordinates of the left-eye position and the right-eye position are registered in the third register.

In step S13, the radiographic image extractor 20 extracts two radiographic images, which are generated by applying radiation from the radiation irradiator 30 at the left-eye position and the right-eye position, from among the radiographic images that are stored in the first storage area 42*a* of the image memory 40, as radiographic images for stereographic vision, i.e., a left-eye radiographic image 112*a* and a right-eye radiographic image 112*b*, and stores the extracted two radiographic images in the third storage area 42*c* of the image memory 40.

In step S14, the image display controller 22 displays the radiographic images for stereographic vision, i.e., the left-eye radiographic image 112*a* and the right-eye radiographic image 112*b*, on the monitor 26, based on a display request for stereographic vision according to an operation input signal from the input device 24. For example, if the display request requests display of the radiographic images in the first display format, then the first stereographic vision display controller 116*a* of the first display format display section 100*a* reads the left-eye radiographic image 112*a* and the right-eye radiographic image 112*b* from the third storage area 42*c* of the image memory 40, and displays the left-eye radiographic image 112*a* and the right-eye radiographic image 112*b* in the second display area 108*b* of the first observational screen 104*a* (see FIG. 5) on the monitor 26. At this time, the radiographic image 109 or the radiographic tomographic image 110, and the left-eye radiographic image 112*a* and the right-eye radiographic image 112*b*, are displayed as multiple images on the first observational screen 104*a*. If the display request requests display of the radiographic images in the second display format, then the second stereographic vision display controller 116*b* of the second display format display section 100*b* reads the left-eye radiographic image 112*a* and the right-eye radiographic image 112*b* from the third storage area 42*c* of the image memory 40, and displays the left-eye radiographic image 112*a* and the right-eye radiographic image 112*b* in the display area 108 of the second observational screen 104*b* (see FIG. 6B) on the monitor 26. At this time, the left-eye radiographic image 112*a* and the right-eye radiographic image 112*b* are displayed in place of the radiographic image 109 or the radiographic tomographic image 110, which has been displayed so far.

With the radiographic image capturing system 10 according to the present embodiment, a position closest to the region 46 of interest, from among a plurality of positions where the tomosynthesis image capturing process is carried out, is selected as a central position, and two positions, which are positionally symmetric with respect to the central position, are determined as two positions for stereographic vision, i.e., a left-eye position and a right-eye position. Then, two radiographic images produced when the radiation irradiator 30 emits radiation 36 toward the subject 34 from the left-eye position and the right-eye position, from among a plurality of radiographic images stored in the first storage area 42*a* of the image memory 40, are extracted as radiographic images for stereographic vision, i.e., a left-eye radiographic image 112*a* and a right-eye radiographic image 112*b*. Consequently, the image of the region 46 of interest established based on the radiographic image 109 or the radiographic tomographic image 110 can be observed effectively by way of stereographic vision. In determining the left-eye radiographic image 112*a* and the right-eye radiographic image 112*b*, two positions, which are connected to the reference coordinates by respective straight lines that are angularly spaced a preset angle θ from a straight line interconnecting the central position and the reference coordinates, are determined as two positions for stereographic vision, i.e., a left-eye position and a right-eye position. The angle θ is established depending on the doctor who observes the images by way of stereographic vision in order to interpret the images. Therefore, the left-eye radiographic image 112*a* and the right-eye radiographic image 112*b* of the region 46 of interest can be displayed for enabling improved stereographic vision by the doctor. Since there is no need for radiographic image capturing processes for stereographic vision after the tomosynthesis image capturing process has been carried out, the subject 34 is prevented from being exposed to an increased dose of radiation. In the first display format, the radiographic image 109 or the radiographic tomographic image 110, which is selected by the operator, and the radiographic images for stereographic vision, i.e., the left-eye radiographic image 112*a* and the right-eye radiographic image 112*b*, are displayed side by side. Consequently, the operator can view the region 46 of interest by way of stereographic vision in comparison with the radiographic image 109 or the radiographic tomographic image 110. In the second display format, the radiographic image 109 or the radiographic tomographic image 110, and the images for stereographic vision are displayed selectively, so that only the images for stereographic vision can be confirmed. The operator can easily switch between the first display format and the second display format, thus making it easy to use the radiographic image capturing system 10 for observing the radiographic image 109 or the radiographic tomographic image 110, along with the images for stereographic vision.

Consequently, the radiographic image capturing system 10 according to the present embodiment is convenient for viewing images by way of stereographic vision and makes it possible to promote widespread use of image observations by way of stereographic vision, while at the same time preventing subjects to be imaged from being exposed to an increased dose of radiation.

Second position determiners according to modifications for use in the radiographic image extractor 20 will be described below with reference to FIGS. 8 through 12.

Figure 8:
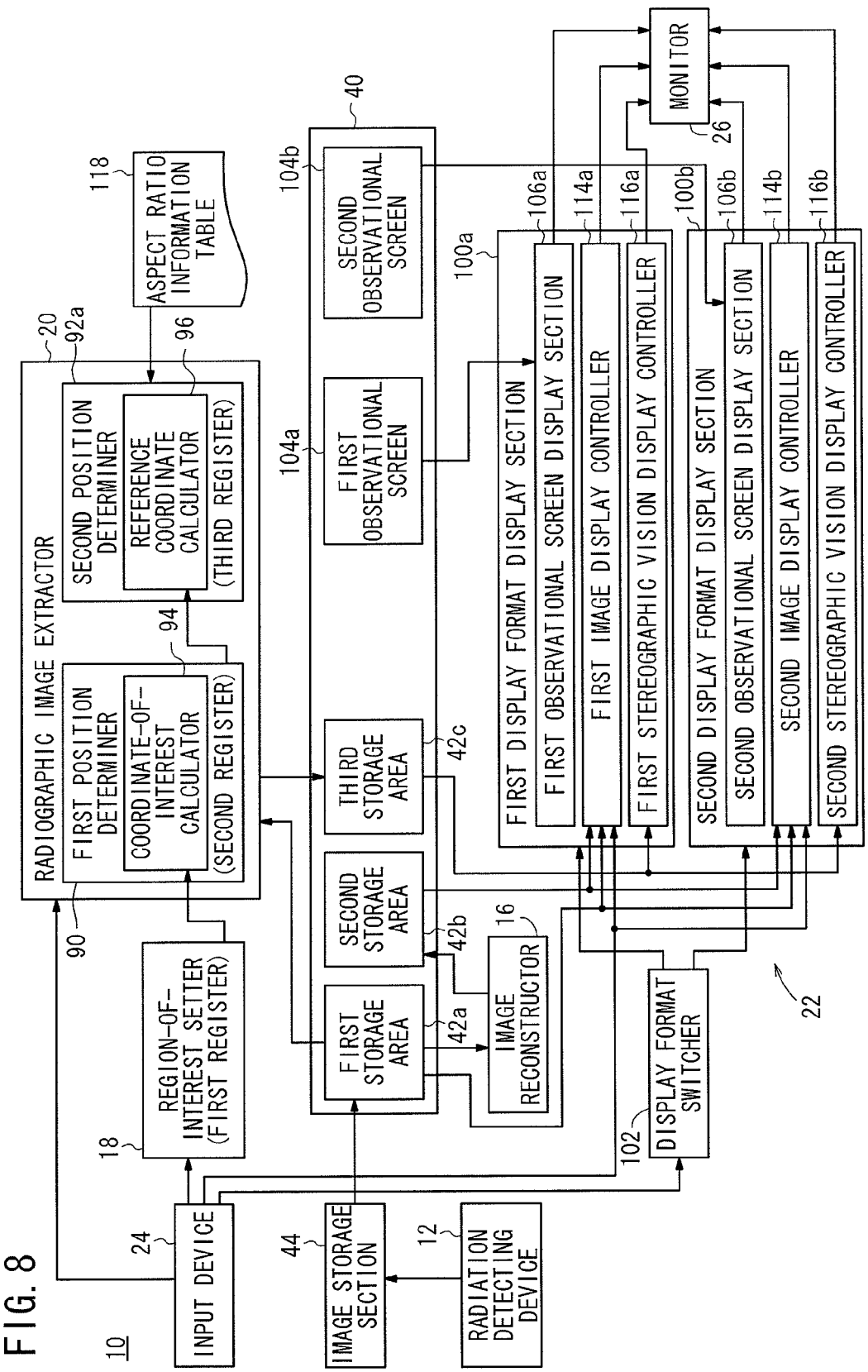
FIG. 8 is a block diagram of a portion of a radiographic image capturing system, which incorporates a second position determiner according to a first modification.
Figure 9:
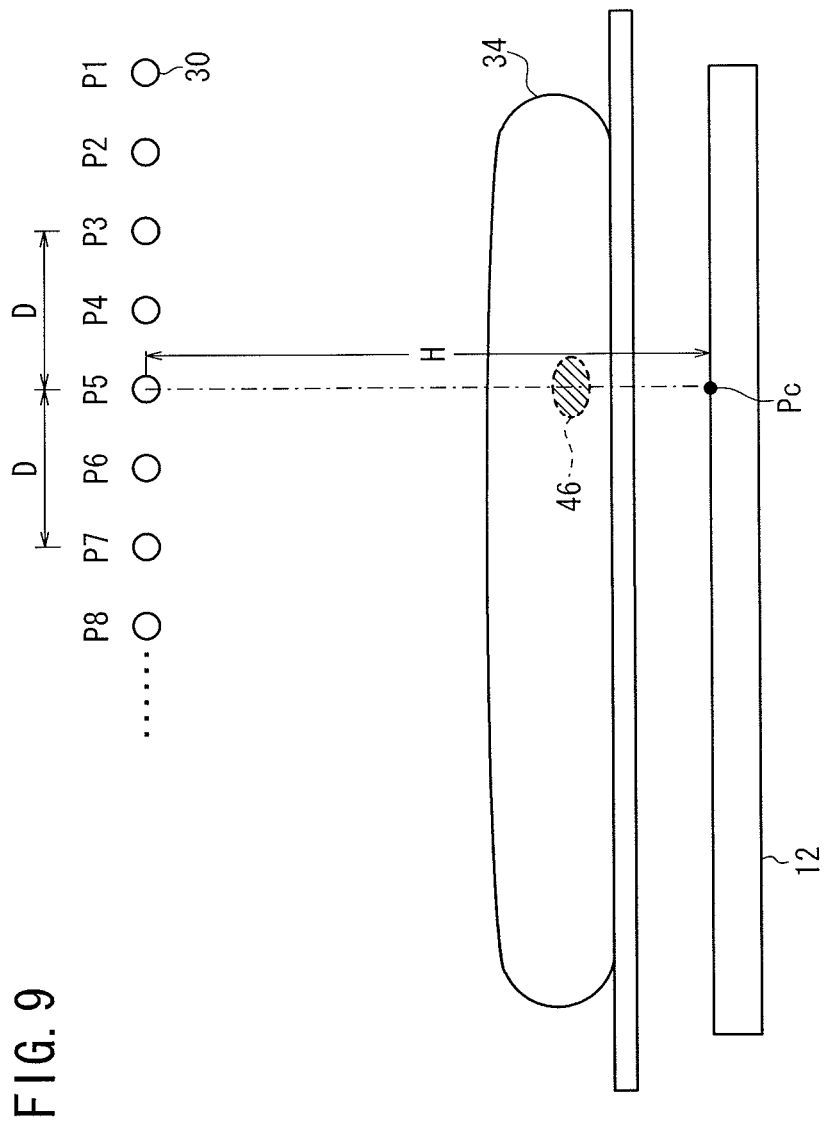
FIG. 9 is a schematic diagram illustrative of a process of determining two positions, i.e., a left-eye position and a right-eye position, with the second position determiner according to the first modification.

As shown in FIGS. 8 and 9, aspect ratios are defined from a vertical distance H from the central position (the position P5 in FIG. 9) determined by the first position determiner 90 to the radiation detecting device 12, and horizontal distances D from the central position to a plurality of positions, i.e., the positions P1, P2, P3, . . . from which the radiation irradiator 30 applies radiation 36. A second position determiner 92*a* according to a first modification decides on two positions, aspect ratios of which satisfy a preset aspect ratio, from among the positions P1, P2, P3, . . . , as two positions for stereographic vision, i.e., a left-eye position and a right-eye position. In FIG. 9, the positions P3, P7, for example, are determined as a left-eye position and a right-eye position.

Since the distance between the left and right eyes varies from individual to individual, aspect ratios are established depending on the doctor who observes images by way of stereographic vision, in the same manner as the angle θ. If there are several doctors who observe images by way of stereographic vision on the radiographic image capturing system 10, then an aspect ratio information table 118 (see FIG. 8) registering therein ID codes and aspect ratios of respective doctors is combined with the radiographic image extractor 20. The second position determiner 92 then reads an aspect ratio depending on an ID code that is entered through the input device 24, i.e., the ID code of the doctor who presently observes images by way of stereographic vision, from the aspect ratio information table 118, and determines a left-eye position and a right-eye position based on the read aspect ratio in the manner described above.

Figure 10:
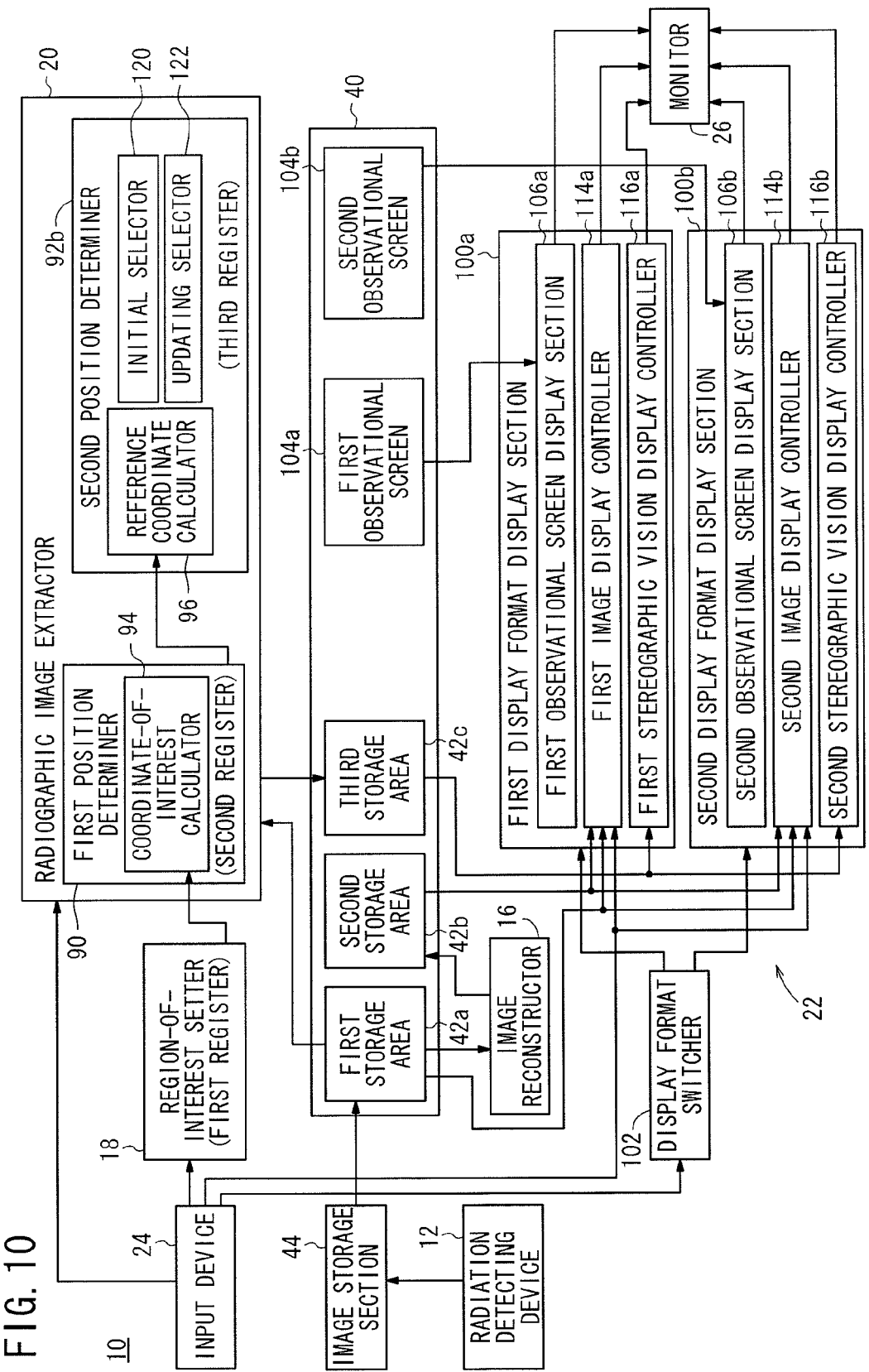
FIG. 10 is a block diagram of a portion of a radiographic image capturing system, which incorporates a second position determiner according to a second modification.

As shown in FIG. 10, a second position determiner 92b according to a second modification includes an initial selector 120 and an updating selector 122, in addition to the reference coordinate calculator 96.

The initial selector 120 selects two positions, which are closest to the central position that initially has been determined by the first position determiner 90, as two positions for stereographic vision, i.e., a left-eye position and a right-eye position. In FIG. 4, since the position P5 is determined as the central position, the initial selector 120 selects positions P4, P6 that are closest to the position P5 as a left-eye position and a right-eye position.

The updating selector 122 selects two positions, which are adjacent, respectively, to the selected two positions, as two positions for stereographic vision, i.e., a left-eye position and a right-eye position, based on an operation input signal (updating request) for updating to next positions from the input device 24. The operation input signal for the updating request may be generated by left-clicking an updating button displayed on the monitor 26, for example. The monitor 26 may display two updating buttons, e.g., a + updating button and a − updating button. When the + updating button is left-clicked, the two positions for stereographic vision may be updated in directions away from the central position. When the − updating button is left-clicked, the two positions for stereographic vision may be updated in directions toward the central position. In FIG. 4, each time the + updating button is left-clicked, the positions P3, P7 and the positions P2, P8 are successively selected. Each time the − updating button is left-clicked after the positions P2, P8 have been selected, the positions P3, P7 and the positions P4, P6 are successively selected.

The second position determiner 92b decides on the selected two positions as two positions for stereographic vision, i.e., a left-eye position and a right-eye position, based on a decisional operation input signal entered from the input device 24.

A processing sequence of the radiographic image capturing system 10, which incorporates the second position determiner 92b according to the second modification, will be described below with reference to the flowcharts shown in FIGS. 11 and 12.

Figure 11:
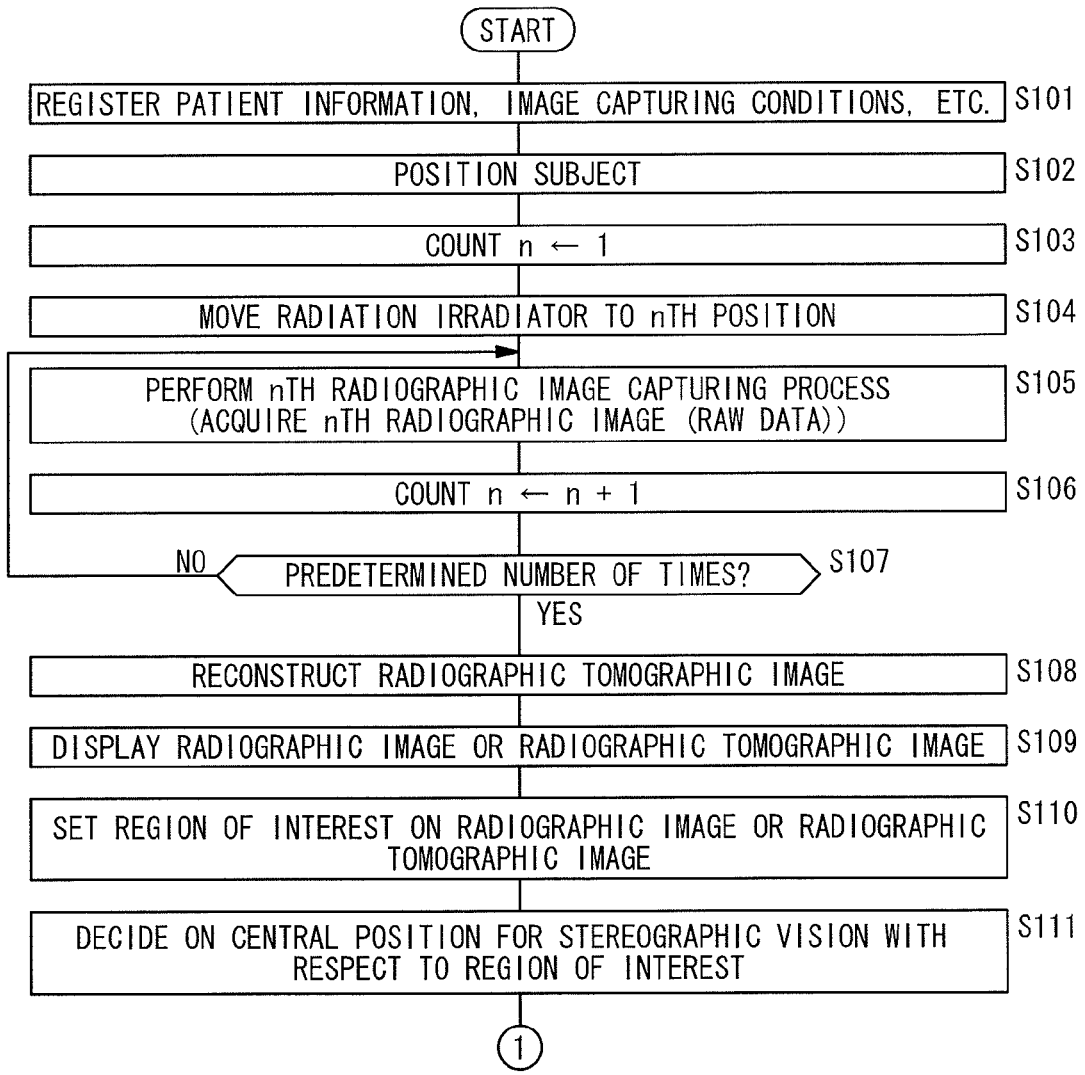
FIG. 11 is a flowchart (first part) of an operation sequence of the radiographic image capturing system, which incorporates the second position determiner according to the second modification.

First, as shown in FIG. 11, in steps S101 through S108, a tomosynthesis image capturing process is carried out, and the generated radiographic images are processed in order to reconstruct a radiographic tomographic image 110. Thereafter, in step S109, the image display controller 22 displays a radiographic image 109 or a radiographic tomographic image 110 on the monitor 26, which is selected by an operation input signal from the input device 24. Then, in step S110, the region-of-interest setter 18 sets a region 46 of interest on the radiographic image 109 or the radiographic tomographic image 110. The first position determiner 90 decides on a central position with respect to the region 46 in step S111.

Figure 12:
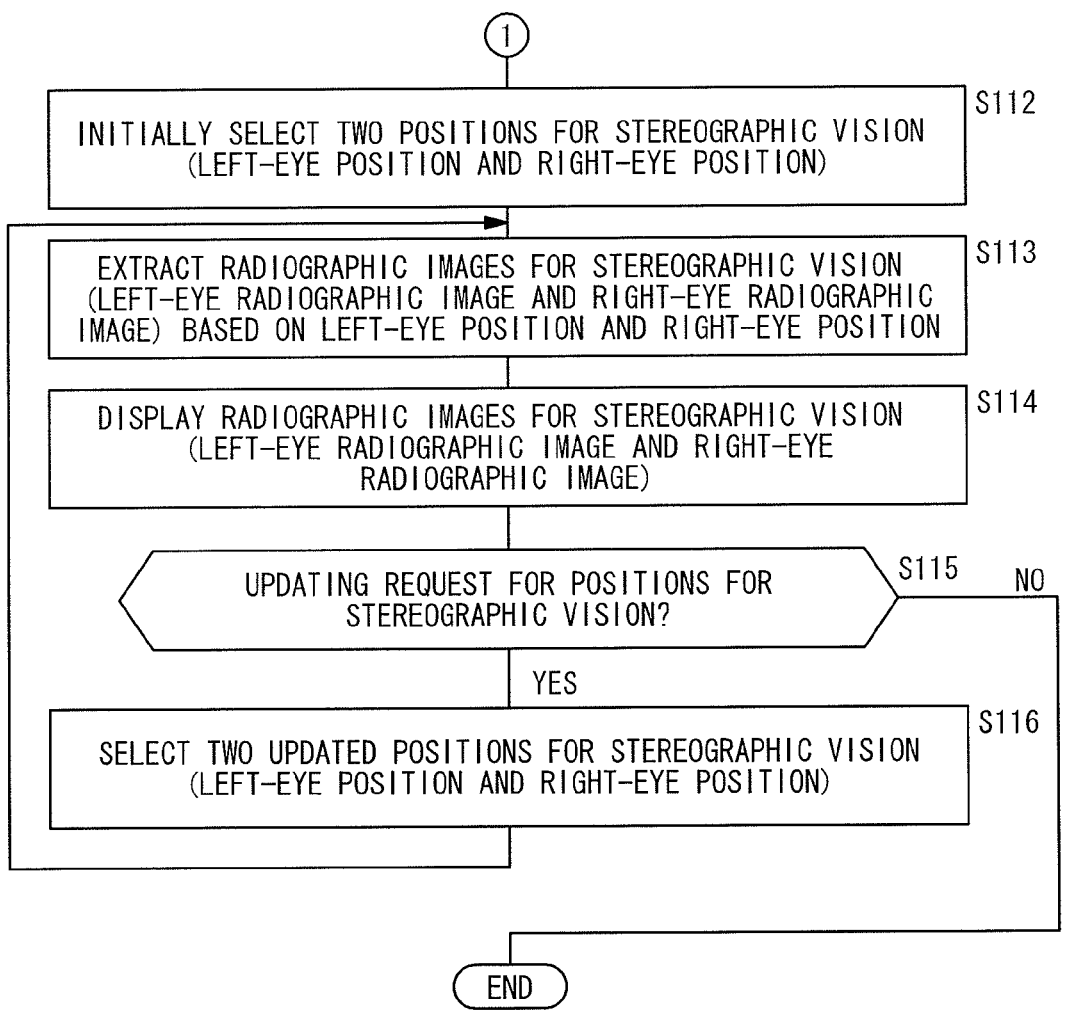
FIG. 12 is a flowchart (second part) of the operation sequence of the radiographic image capturing system, which incorporates the second position determiner according to the second modification.

In step S112 shown in FIG. 12, the initial selector 120 of the second position determiner 92b initially selects two positions, which are closest to the central position determined by the first position determiner 90, from among the positions P1, P2, P3, . . . from which the radiation irradiator 30 applies radiation 36 during the tomosynthesis image capturing process, as two positions for stereographic vision, i.e., a left-eye position and a right-eye position.

Thereafter, in step S113, the radiographic image extractor 20 extracts two radiographic images, which are generated by applying radiation from the radiation irradiator 30 at the left-eye position and the right-eye position, from among the radiographic images that are stored in the first storage area 42a of the image memory 40, as radiographic images for stereographic vision, i.e., a left-eye radiographic image 112a and a right-eye radiographic image 112b, and stores the extracted two radiographic images in the third storage area 42c of the image memory 40.

In step S114, the image display controller 22 displays the radiographic images for stereographic vision, i.e., the left-eye radiographic image 112a and the right-eye radiographic image 112b, on the monitor 26, based on a display request for stereographic vision according to an operation input signal entered from the input device 24.

In step S115, it is determined whether there is an updating request or a deciding request with respect to the selected two positions for stereographic vision, by determining whether an operation input signal from the input device 24 represents an updating request or a deciding request.

If the operation input signal represents an updating request, then control proceeds to step S116, in which the updating selector 122 selects two positions, which are adjacent respectively to the selected two positions, as two updated positions for stereographic vision, i.e., a left-eye position and a right-eye position. Thereafter, control returns to step S113, and steps S113 through S116 are repeated.

If the operation input signal represents a decision request in step S115, the processing sequence of the radiographic image capturing system 10 is brought to an end.

With the radiographic image capturing system 10 that incorporates therein the second position determiner 92b according to the second modification, two positions closest to the central position initially are selected, and radiographic images for stereographic vision are extracted and displayed based on the selected two positions. Based on subsequent updating requests, the two positions are successively updated, and radiographic images for stereographic vision are extracted and displayed based on the successively updated two positions. Consequently, the operator, i.e., a doctor who interprets radiographic images, can decide on radiographic images for stereographic vision, which are believed to be optimum or preferable (not inadequate) for image interpretation. Thus, the radiographic image capturing system 10 incorporating the second position determiner 92b is convenient for viewing the radiographic tomographic image 110 and the radiographic images by way of stereographic vision.

In the above embodiment, the radiographic tomographic image 110 and the radiographic images for stereographic vision can selectively be displayed in the first display format and the second display format. However, such images may be displayed in the first display format or the second display format only.

The second position determiner 92 may decide on two positions based on the angle (see FIGS. 2 and 4), the aspect ratio (see FIGS. 8 and 9), or based on updating of the position (see FIGS. 10 through 12), which may be selected according to an operation input signal from the input device 24 operated by the operator, i.e., a doctor who interprets the images.

The radiation detector 54 of the radiation detecting device 12 is of a direct conversion type, which directly converts the dose of applied radiation 36 into an electric signal with the photoelectric conversion layer 58. However, the radiation detector 54 may be of an indirect conversion type for converting applied radiation 36 into an electric signal with a solid-state detecting device, such as a solid-state detecting device made up of amorphous silicon (a-Si) or the like (see Japanese Patent No. 3494683).

Alternatively, the radiographic image generating system may employ a light-readout radiation detector for acquiring radiographic image information. Such a light-readout radiation detector operates in the following manner. When radiation is applied to a matrix of solid-state detecting devices, the solid-state detecting devices store an electrostatic latent image depending on the dose of applied radiation. For reading the stored electrostatic latent image, reading light is applied to the solid-state detecting devices to cause the solid-state detecting devices to generate an electric current representing radiographic image information. When erasing light is applied to the radiation detector, radiographic image information representing a residual electrostatic latent image is erased from the radiation detector, which can thus be reused (see Japanese Laid-Open Patent Publication No. 2000-105297).

While the illustrated radiation detector 54 employs TFTs 60, a radiation detector may employ any of various other image capturing devices, such as a CMOS (Complementary Metal-Oxide Semiconductor) image sensor or a CCD (Charge-Coupled Device) image sensor, wherein electric charges are shifted and transferred by shift pulses that correspond to gate signals used in the TFTs 60.

Although certain preferred embodiments of the present invention have been shown and described in detail, it should be understood that various changes and modifications may be made to the embodiments without departing from the scope of the invention as set forth in the appended claims.

What is claimed is:

1. A radiographic image capturing system comprising:
a radiation detecting device;
a radiographic image acquirer configured to move a radiation irradiator disposed in confronting relation to the radiation detecting device successively to a plurality of positions, and controlling the radiation irradiator to apply radiation from the positions along respective different directions to a subject disposed over the radiation detecting device, for acquiring a plurality of respective radiographic images from the radiation detecting device;
an image reconstructor configured to process the radiographic images acquired by the radiographic image acquirer to reconstruct a radiographic tomographic image of the subject;
a display device configured to display at least the radiographic images;
an input device operable by an operator of the radiographic image capturing system;
a region-of-interest setter configured to set a region of interest of the subject for stereographic vision;
a radiographic image extractor configured to extract, from among the radiographic images, two radiographic images for viewing the region of interest by way of stereographic vision; and
a stereographic vision display controller configured to control the display device to display the extracted two radiographic images for stereographic vision,
wherein the region-of-interest setter sets the region of interest based on an operation input signal from the input device,
wherein the radiographic image extractor comprises:
a first position determiner configured to decide on one position serving as a center for stereographic vision from among the positions from which the radiation irradiator applies radiation, based on coordinates of the region of interest; and
a second position determiner configured to decide on two positions, which are positionally symmetric with respect to the one position decided on by the first position determiner, from among the positions from which the radiation irradiator applies radiation;
wherein the radiographic image extractor extracts, as the two radiographic images, radiographic images generated when the radiation irradiator applies radiation from the two positions, from among the radiographic images acquired by the radiographic image acquirer; and
wherein the first position determiner comprises:
a coordinate-of-interest calculator configured to determine plane coordinates on the radiation detecting device, which correspond to the coordinates of the region of interest;
wherein the first position determiner decides on a position, plane coordinates of which are closest to the determined plane coordinates on the radiation detecting device, from among the positions from which the radiation irradiator applies radiation, as the one position serving as the center for stereographic vision; and
wherein the operation input signal for setting the region of interest comprises a set of two dimensional coordinates set according to the center of a frame around an image of the region of interest, the frame enclosing a subset of a displayed radiographic image or a displayed radiographic tomographic image, said subset being disposed at a selectable position within the displayed image.

2. The radiographic image capturing system according to claim 1, further comprising:
an image display controller configured to control the display device to display a radiographic image, which is selected from among the radiographic images acquired by the radiographic image acquirer, based on an operation input signal from the input device;
wherein the region-of-interest setter sets the region of interest on the selected radiographic image.

3. The radiographic image capturing system according to claim 1, further comprising:
an image display controller configured to control the display device to display a radiographic tomographic image of a body section of the subject, which is selected from among radiographic tomographic images reconstructed by the image reconstructor, based on an operation input signal from the input device;
wherein the region-of-interest setter sets the region of interest on the selected radiographic tomographic image.

4. The radiographic image capturing system according to claim 1, wherein the second position determiner comprises:
a reference coordinate calculator configured to determine plane coordinates as reference coordinates on the radiation detecting device, which correspond to the one position as the center for stereographic vision;
wherein the second position determiner decides on two positions, which are positionally symmetric with respect to the one position, and which are connected to the reference coordinates by respective straight lines that are angularly spaced a preset angle from a straight line interconnecting the one position and the reference coordinates, from among the positions from which the radiation irradiator applies radiation, as two positions for stereographic vision.

5. The radiographic image capturing system according to claim 1, wherein the second position determiner decides on two positions, where aspect ratios defined from a vertical distance from the one position to the radiation detecting device and horizontal distances from the one position to the positions from which the radiation irradiator applies radiation satisfy a preset aspect ratio, as two positions for stereographic vision.

6. The radiographic image capturing system according to claim 1,
wherein the second position determiner comprises:
an initial selector configured to initially select two positions closest to the one position as two positions for stereographic vision; and
an updating selector configured to select two positions adjacent to the initially selected two positions as two updated positions for stereographic vision based on an operation input signal for updating to next positions from the input device; and
wherein the second position determiner decides on the selected two positions as two positions for stereographic vision based on an operation input signal for deciding from the input device.

7. The radiographic image capturing system according to claim 2, wherein the image display controller controls the display device to switch between displaying the selected radiographic image and displaying the extracted two radiographic images, based on an operation input signal from the input device.

8. The radiographic image capturing system according to claim 2, wherein the image display controller controls the display device to display the selected radiographic image in a first display area; and
the stereographic vision display controller controls the display device to display the extracted two radiographic images in a second display area.

9. The radiographic image capturing system according to claim 3, wherein the image display controller controls the display device to switch between displaying the selected radiographic tomographic image and displaying the extracted two radiographic images, based on an operation input signal from the input device.

10. The radiographic image capturing system according to claim 3, wherein the image display controller controls the display device to display the selected radiographic tomographic image in a first display area; and
the stereographic vision display controller controls the display device to display the extracted two radiographic images in a second display area.

11. A method of displaying radiographic images in a radiographic image capturing system including a radiation detecting device, a radiographic image acquirer for moving a radiation irradiator disposed in confronting relation to the radiation detecting device successively to a plurality of positions, and controlling the radiation irradiator to apply radiation from the positions along respective different directions to a subject disposed over the radiation detecting device, for acquiring a plurality of respective radiographic images from the radiation detecting device, an image reconstructor for processing the radiographic images acquired by the radiographic image acquirer to reconstruct a radiographic tomographic image of the subject, a display device for displaying at least the radiographic images, and an input device operable by an operator of the radiographic image capturing system, the method comprising the steps of:
setting a region of interest of the subject for stereographic vision;
extracting, from among the radiographic images, two radiographic images for viewing the region of interest by way of stereographic vision; and
controlling the display device to display the extracted two radiographic images for stereographic vision,
wherein the step of setting the region of interest sets the region of interest based on an operation input signal from the input device,
wherein the step of extracting the radiographic images comprises the steps of:
determining a first position for deciding on one position serving as a center for stereographic vision from among the positions from which the radiation irradiator applies radiation, based on coordinates of the region of interest; and
determining a second position for deciding on two positions, which are positionally symmetric with respect to the one position decided on by the first position determiner, from among the positions from which the radiation irradiator applies radiation,
wherein the step of extracting the radiographic images extracts, as the two radiographic images, radiographic images generated when the radiation irradiator applies radiation from the two positions, from among the radiographic images acquired by the radiographic image acquirer,
wherein the step of determining the first position comprises a step of calculating a coordinate-of-interest for determining plane coordinates on the radiation detecting device, which correspond to the coordinates of the region of interest, and
wherein the step of determining the first position decides on a position, plane coordinates of which are closest to the determined plane coordinates on the radiation detecting device, from among the positions from which the radiation irradiator applies radiation, as the one position serving as the center for stereographic vision, and
wherein the operation input signal for setting the region of interest comprises a set of two dimensional coordinates set according to the center of a frame around an image of the region of interest, the frame enclosing a subset of a displayed radiographic image or a displayed radiographic tomographic image, said subset being disposed at a selectable position within the displayed image.

12. The method according to claim 11, further comprising the step of:
controlling the display device to display a radiographic image, which is selected from among the radiographic images acquired by the radiographic image acquirer, based on an operation input signal from the input device;
wherein the step of setting the region of interest sets the region of interest on the selected radiographic image.

13. The method according to claim 11, further comprising the step of:
controlling the display device to display a radiographic tomographic image of a body section of the subject, which is selected from among radiographic tomographic images reconstructed by the image reconstructor, based on an operation input signal from the input device;
wherein the step of setting the region of interest sets the region of interest on the selected radiographic tomographic image.

14. The method according to claim 12, further comprising the step of:
controlling the display device to switch between displaying the selected radiographic image and displaying the extracted two radiographic images, based on an operation input signal from the input device.

15. The method according to claim 12, wherein the step of controlling the display device to display a radiographic image displays the selected radiographic image in a first display area, and the step of controlling the display device to display the extracted two radiographic images displays the extracted two radiographic images in a second display area.

16. The method according to claim 13, further comprising the step of:
   controlling the display device to switch between displaying the selected radiographic tomographic image and displaying the extracted two radiographic images, based on an operation input signal from the input device.

17. The method according to claim 13, wherein the step of controlling the display device to display a radiographic image displays the selected radiographic tomographic image in a first display area, and the step of controlling the display device to display the extracted two radiographic images displays the extracted two radiographic images in a second display area.

* * * * *